US012751762B2

(12) United States Patent
Knopf et al.

(10) Patent No.: US 12,751,762 B2
(45) Date of Patent: Oct. 6, 2026

(54) ELECTRODE FOR AN ELECTROSURGICAL HANDHELD INSTRUMENT

(71) Applicant: OLYMPUS WINTER & IBE GMBH, Hamburg (DE)

(72) Inventors: Christoph Knopf, Stockelsdorf (DE); Christian Brockmann, Hollenstedt (DE); Jiri Lavicka, Prerov (CZ); Petr Kominek, Prerov (CZ)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 192 days.

(21) Appl. No.: 18/402,074

(22) Filed: Jan. 2, 2024

(65) Prior Publication Data

US 2024/0225721 A1 Jul. 11, 2024

Related U.S. Application Data

(60) Provisional application No. 63/437,157, filed on Jan. 5, 2023.

(51) Int. Cl.
*A61B 18/14* (2006.01)

(52) U.S. Cl.
CPC .... *A61B 18/1485* (2013.01); *A61B 2018/144* (2013.01)

(58) Field of Classification Search
CPC ... A61B 18/1485; A61B 18/149; A61B 18/14; A61B 2018/144; A61B 2018/1405; A61B 2018/00505
USPC .......................................................... 606/41
See application file for complete search history.

(56) References Cited

U.S. PATENT DOCUMENTS

| | | | | | |
|---|---|---|---|---|---|
| 5,569,244 | A * | 10/1996 | Hahnen | A61B 18/149 | 606/49 |
| 5,919,190 | A * | 7/1999 | VanDusseldorp | A61B 18/149 | 606/49 |
| 5,919,191 | A * | 7/1999 | Lennox | A61B 18/149 | 606/50 |
| 6,197,025 | B1 * | 3/2001 | Grossi | A61B 18/149 | 606/49 |
| 6,245,069 | B1 * | 6/2001 | Gminder | A61B 18/149 | 606/45 |

(Continued)

FOREIGN PATENT DOCUMENTS

| | | | |
|---|---|---|---|
| CN | 115137473 | A | 10/2022 |
| DE | 100 28 850 | C1 | 10/2001 |

(Continued)

OTHER PUBLICATIONS

Oct. 21, 2025 Office Action issued in Japanese Patent Application No. 2024-003443.

*Primary Examiner* — Beverly M Flanagan
(74) *Attorney, Agent, or Firm* — Oliff PLC

(57) ABSTRACT

An electrode for an electrosurgical handheld instrument consists of an electrically conductive wire, the two ends of the wire being connectable to an electrode carrier of the handheld instrument. In this case, the wire has two portions R1 and L1, which are adjacent to the two ends of the wire and are aligned parallel to one another and rectilinearly. Two second portions R2 and L2 follow on from these two first portions R1 and L1, these two portions R2 and L2 being connected to one another by a portion C. This portion C in turn has a flattened portion CC.

11 Claims, 2 Drawing Sheets

(56) References Cited

U.S. PATENT DOCUMENTS

| | | | |
|---|---|---|---|
| 7,429,262 B2 | 9/2008 | Woloszko et al. | |
| 2001/0025177 A1 | 9/2001 | Woloszko et al. | |
| 2001/0053908 A1 | 12/2001 | Brommersma et al. | |
| 2003/0130653 A1* | 7/2003 | Sixto, Jr. ............ | A61B 18/1482 606/45 |
| 2005/0251134 A1* | 11/2005 | Woloszko ............ | A61B 18/149 606/46 |
| 2017/0076445 A1 | 3/2017 | Hu | |
| 2019/0021786 A1* | 1/2019 | Ward ................... | A61B 18/149 |

FOREIGN PATENT DOCUMENTS

| | | |
|---|---|---|
| DE | 10 2020 118 265 A1 | 1/2022 |
| EP | 2 767 250 B1 | 7/2018 |
| JP | 2008-220988 A | 9/2008 |
| JP | 2015-228954 A | 12/2015 |
| JP | 2017-146758 A | 8/2017 |
| JP | 2017-532078 A | 11/2017 |
| JP | 2019-161558 A | 9/2019 |
| WO | 98/7377 A1 | 2/1998 |
| WO | 2020/249236 A1 | 12/2020 |

* cited by examiner

ELECTRODE FOR AN ELECTROSURGICAL HANDHELD INSTRUMENT

TECHNICAL FIELD

The invention relates to an electrode for an electrosurgical handheld instrument according to the preamble of claim 1.

BACKGROUND

Electrosurgical handheld devices, in particular resectoscopes, of the type in question are used above all for electrosurgical operations in urology. In this case, these devices are conventionally used for the resection and evaporation of tissue, for example tissue in the lower urinary tract. For this purpose the handheld instrument, in particular the resectoscope, may have a length-adjustable electrode carrier which, after the insertion of the device with a distal working end into the body to be treated, can be displaced forward from a distal end of the instrument shaft of the handheld device. An electrosurgical electrode is arranged at a distal end on the electrode carrier. This electrode may for example have the shape of a loop, and in order to manipulate the tissue is pulled or pushed through the tissue, depending on the design of the instrument.

Known electrodes are formed from a wire with a circular cross section. For loop electrodes, for example, it is known that the wire with the circular cross section is formed into a loop and the two free ends are connected to the electrode carrier. By the application of the radiofrequency alternating voltage, a plasma is ignited on the electrode so that a plasma is formed on the wire in interaction with the fluid surrounding the electrode. The plasma is preferentially ignited at positions of the electrode which have a small radius of curvature, since the electric field strength is greatest there. In the case of a continuous wire as the electrode, with a constant cross section, the plasma is ignited with a statistical distribution over the entire length of the electrode. A preferential position for the plasma ignition cannot therefore be established. This proves disadvantageous for the manipulation of the body tissue, however, since the plasma is only rarely and therefore not reliably ignited at a particular position of the electrode, i.e. it is ignited randomly. Furthermore, the contact area of the loop electrode with the tissue is small because of its circular cross section, so that the coagulation performance is inferior compared with other electrode shapes.

In another known embodiment of an electrode, the so-called band electrode, a single loop with a rectangular cross section is initially produced and this loop is then welded at its two ends to short wires, which are in turn to be coupled to the electrode carrier. Such electrodes are also found to be particularly elaborate and cost-intensive, especially in terms of their production. With these band electrodes as well, furthermore, the plasma is not ignited preferentially at one position but is ignited with a statistical distribution over the entire length and therefore also at less advantageous positions, for example at the transitions to the wires.

For the production of known electrodes, tubes which are compressed so that the cross section is configured ovally are therefore used. Because of the different radii of curvature of the compressed tube, regions with a different field strength are generated along the tube and regions at which the plasma is preferentially ignited are therefore provided. This type of electrode, however, is particularly cost-intensive in terms of its production since, in particular, thin tubes or tubelets made of materials such as a platinum-iridium alloy are very expensive.

SUMMARY

It is therefore an object of the invention to provide an electrode which can be used particularly efficiently and can be produced in a particularly economical way.

A solution to this object is described by claim 1. Accordingly, an electrode for an electrosurgical handheld instrument, in particular for a resectoscope, consists of an electrically conductive wire, the two ends of the wire being connectable to an electrode carrier of the handheld instrument. The wire in this case has two portions R1 and L1, which are adjacent to the two ends of the wire and are aligned parallel to one another and rectilinearly. Two second portions R2 and L2 follow on from these two first portions R1 and L1, these two portions R2 and L2 being connected to one another by a portion C. This portion C in turn has a flattened portion CC. This flattened portion CC may be identical to the length of the portion C or constitute only a small portion of C.

Preferably, according to the invention, the wire has a round or circular cross section and the flattened portion CC has an oval or elliptical cross section or a rectangular cross section with rounded corners. The cross section of the portion CC therefore differs from the cross sections of the other wire portions insofar as it has different radii of curvature. In this case, the cross section of the portion C is configured in such a way that it has a smallest radius of curvature in relation to all other portions of the wire. This smallest radius of curvature is restricted to the portion C, or the portion CC. Since the plasma is ignited, or breaks through the gas phase, preferentially and particularly rapidly where the electric field strength is the greatest, the probability of the plasma ignition is greatest here. Since this constitutes only a limited portion of the wire, the electrode may be used particularly expediently and reliably for the manipulation of the tissue. A further advantage of the feature is that the electrode is produced from a wire that on the one hand is very favorable in terms of its procurement and furthermore is particularly easy to shape, or handle.

In particular, according to the invention, the portions R1 and L1 and the portions R2 and L2 may have a round or circular cross section. If the portion CC occupies only a part of the portion C, the unflattened part of the portion C likewise has a round or circular cross section. Owing to this shape of the other portions, on which the electric field strength is rather low because of the consistent shape of the cross section, very rapid and reliable ignition of the plasma in the portion C, or CC, may be additionally promoted.

Further, it is conceivable for the portion C to have a radius of from 2.8 mm to 3.5 mm or to be rectilinear or to be aligned at a right angle to the portions R2 and L2 or to have a V-shape. Depending on the type of electrode or field of use, the portion C may be configured in a different way. In the case of a loop electrode, however, the portion C or the portion CC is shaped like a segment of a circle and may, for example, include an angle ω of from 110° to 160° between the two portions R2 and L2. In this case, only the portion CC with the aforementioned radius is flattened. At the transition from the portion CC to the portion C, or from the portion C to the portions R2 and L2, the cross-sectional shape of the wire transitions continuously from the flattened shape into the circular shape.

Furthermore, according to the invention, the portions R2 and L2 may also have a radius or be aligned parallel to one another and/or the transitions between the portions L1 and L2, R1 and R2 and between C and L2 and R2 may have a radius. It is in this case conceivable for the radius of the portions R2 and L2 likewise to lie in the range of from 2.8 mm to 3.5 mm or to differ from the radius of the portion C. By a radius of the portions R2 and L2, the transition of the various cross-sectional shapes from the portions R2 and L2 to the portion C may optionally be made smoother so that no radii of curvature that are smaller than the smallest radius of curvature of the portion C are formed at these transition locations. Likewise, it is also conceivable for the two portions R2 and L2 to be aligned parallel to one another and rectilinearly and on the one hand preferably to lie in the same plane as the portions R1 and L1 and on the other hand to lie in the same plane as the portion C.

According to a particularly advantageous exemplary embodiment of the invention, the wire may have a diameter of from 0.4 mm to 0.6 mm, preferably 0.5 mm. The cross section of the flattened portion CC has a height-to-width ratio of from 1:1.5 to 1:4, preferably 1:2. According to one particularly preferred exemplary embodiment, a height of the flattened portion CC is 0.3 mm and a width is 0.6 mm. In this case, it should explicitly be pointed out that the corners of the flattened cross section, or of the rectangular cross section, are round so that a cross section having a continuous contour is formed rather than a rectangle. By this shape, a plasma is particularly preferentially formed around the portion CC, or on the regions of the portion CC with the least radius of curvature.

It is known that in the course of the use of the electrode, material erosions that may lead to a change in the shape of the electrode occur. This may be avoided by the shape of the portion CC as described here. Because of the rounded shape of the flattened portion CC, the material wear is distributed over the entire length, or over the entire circumference, of the wire so that the electrode can be used with the required reliability for a longer period of time.

According to another preferred exemplary embodiment of the invention, the wire may be formed from tungsten, stainless steel, platinum-iridium, titanium, a titanium alloy or a platinum-tungsten alloy. These materials can be particularly advantageous since they are electrically conductive, have a high electrical and mechanical stability and a high resistance to plasma erosion and are mechanically easy to process, or form.

Further, according to the invention, the lengths of the portions R2 and L2 may be from 0.7 mm to 1.7 and the two second portions R2 and L2 may include an angle $\alpha$ of from 35° to 120°, preferably 90°, 45° or 110°, with the first portions R1 and L1. In this case, the portions R2, L2 and C and CC may furthermore lie in a common plane. It has been found that this dimensioning and these relative arrangements are particularly advantageous for efficient treatment of the patient and for particularly economical production of the electrode. Depending on the nature of the use of the electrode, different angles may be selected between the two portion pairs. The portions R1 and R2 as well as L1 and L2 respectively lie in a plane, these planes being aligned parallel to one another. By this shaping according to the invention of the various portions, a multiplicity of different electrode shapes may be produced particularly simply and therefore economically. Furthermore, according to another exemplary embodiment of the invention, bending radii between the portions R1 and R2 as well as L1 and L2 may be from 0.1 mm to 1 mm.

A preferred exemplary embodiment of the invention will be described in more detail below with the aid of the drawing, in which:

DETAILED DESCRIPTION

Figure 1:
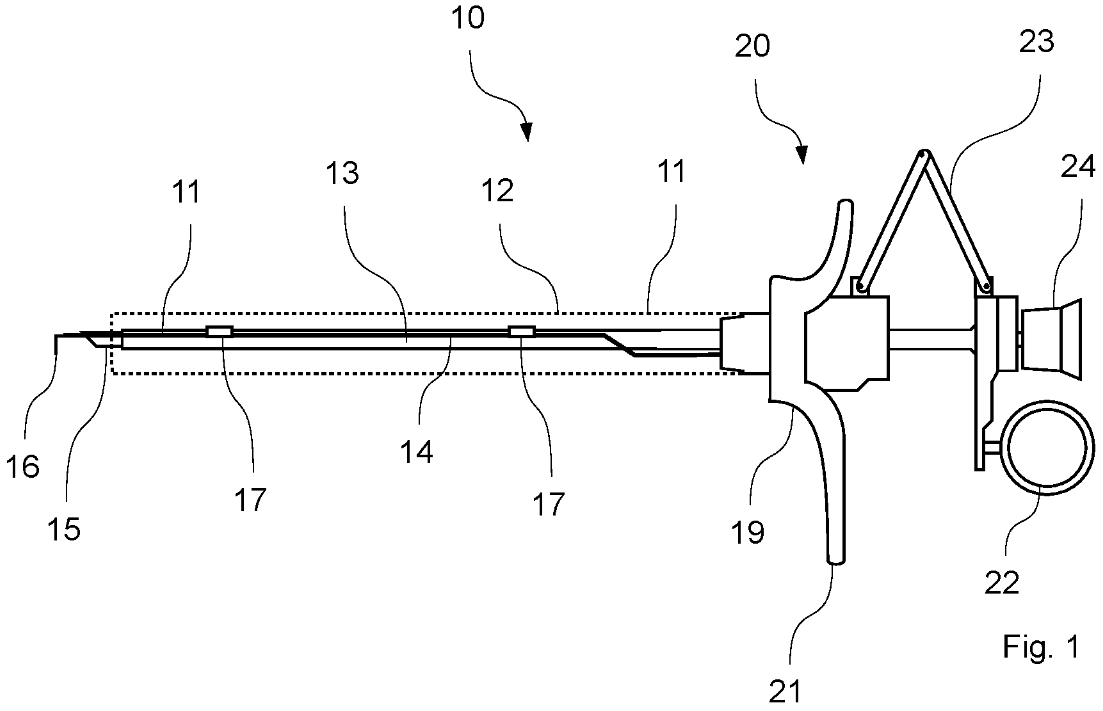
FIG. 1 shows a schematic representation of a surgical handheld device, in particular a resectoscope.

FIG. 1 shows a schematic lateral sectional representation of a known resectoscope 10. The resectoscope 10 has a resectoscope shaft 11, which comprises an outer shaft 12, or a cover tube. A tubular inner shaft 13 runs inside the outer shaft 12. Represented inside the inner shaft 13 are an electrode carrier 14 and optics 15 (merely indicated). Other elements (not represented here) may furthermore be arranged in the resectoscope 10, for example a separate rinsing tube and the like.

At a distal end, the electrode carrier 14 has an electrosurgical tool, or an electrode 16. The electrode 16 represented here is depicted as a loop, although it may also be configured as a knob or the like.

By actuating a handle 19, the electrode carrier 14 can be moved while being forcibly guided axially in the distal and proximal directions. It may in this case be deployed beyond the distal end of the inner shaft 13 and the outer shaft 12. This allows the operator to manipulate tissue even further removed from the resectoscope tip. For this purpose, the inner shaft 13 and/or the electrode carrier 14 may further be mounted rotatably about their longitudinal axis. For the manipulation of the tissue, a radiofrequency electrical current is applied to the electrode 16.

The resectoscope 10 represented in FIG. 1 has a passive transporter, in which a slide 20 is displaced by relative movement of the grip parts 21 and 22 arranged approximately on the resectoscope shaft 11 against a spring force applied by a spring bridge 23 in the distal direction against the distal first grip part 21. During the displacement of the slide 20 in the distal direction against the grip part 21, the electrode carrier 14 is displaced (in a manner not represented) in the distal direction. When the handle parts 21, 22 are released, the spring force generated by the spring bridge 23 forces the slide 20 back into its initial position, the electrode carrier 14 being pulled in the proximal direction. During the return displacement of the slide 20, an electrosurgical intervention with the electrode 16 may be carried out without manual force from the operator, that is to say passively.

For expedient treatment by means of the electrode 16, the optics 15 are positioned in such a way that the operator is provided with an optimal view of the region of the operation. For this purpose, the resectoscope 10 has, at a proximal end, an eyepiece 24 which is connected to the optics 15. Alternatively, it is also conceivable for a camera to be arranged on the resectoscope 10 instead of the eyepiece 24.

Figure 2:
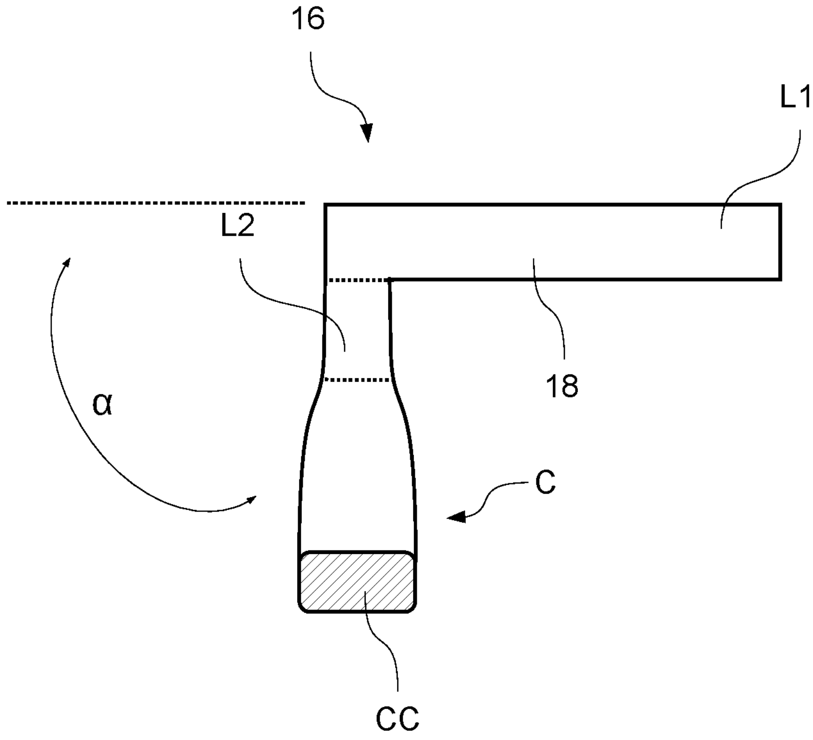
FIG. 2 shows a lateral view of an electrode.
Figure 3:
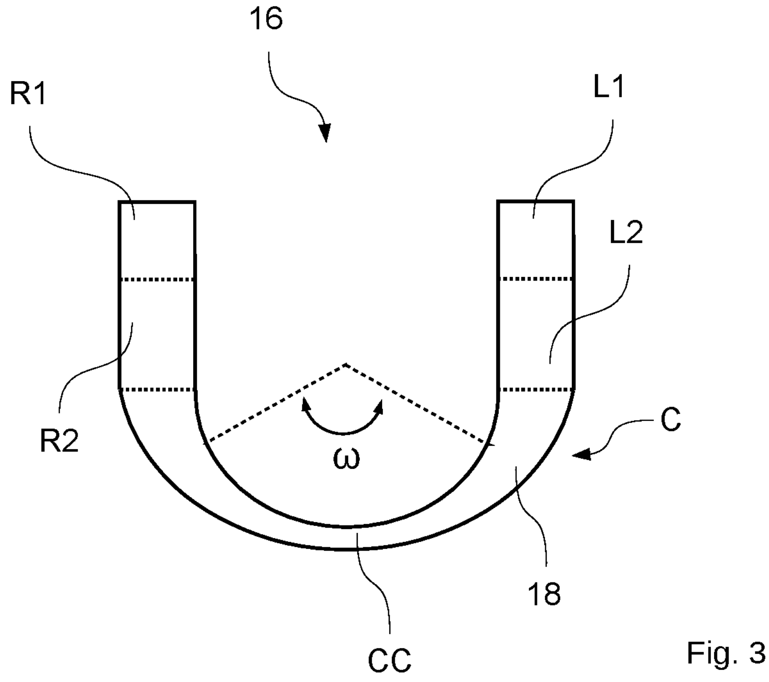
FIG. 3 shows a front view of the electrode.

FIGS. 2 and 3 represent an exemplary embodiment of an electrode 16 according to the invention. This electrode 16 has a first proximal portion of the wire R1 and a second proximal portion of the wire L1, the first portions R1 and L1 being equally long and aligned parallel to one another. These first portions R1 and L1 are connected to the distal ends of the electrode carrier tubes. By this connection or coupling to the electrode carrier tubes, the electrode 16 is stabilized and is supplied with electrical energy. A first distal portion of the wire R2 and a second distal portion of the wire L2 follow on from the first portions R1 and L1. These two second portions R2 and L2 are likewise configured to be equally long and aligned parallel to one another. The transition from the first portions R1 and L1 to the second portions R2 and L2 takes place in a plane. In the exemplary embodiment of the electrode 16 as represented here, the second portions R2 and L2 are inclined relative to the first portions R1 and L1 by an angle of 90°. It is, however, also conceivable for this angle α to have a value of between 35° and 120°, preferably 45°, 90° or 110°, or any other angle.

A central portion of the wire C is located between the two second portions R2 and L2. This portion C connects the two second portions R2 and L2 and, in the exemplary embodiment represented, is configured as a loop. The shape of the portion C may likewise vary and, for example, have a larger or smaller radius of curvature. In the present exemplary embodiment, the portion C lies in the same plane as the portions R2 and L2. In order to carry out the operation, depending on the type of resectoscope 10, the electrode 16 is pulled or pushed with the portion C through the tissue to be treated.

According to the invention, the electrode 16 consists of a wire 18, preferably a wire 18 made of tungsten, stainless steel, platinum-iridium, titanium, a titanium alloy or a platinum-tungsten alloy. This wire 18, and in particular the portions L1 and L2 as well as R1 and R2, and optionally also sections of the portion C, have a round or circular cross section (FIG. 2, 3). According to the invention, the wire 18 has a flattened portion of the wire CC in the portion C. In this portion CC, the otherwise circular wire 18 is figuratively speaking pressed flat so that the cross section is not circular but instead oval, elliptical or describes a rectangle with rounded corners. This cross-sectional shape of a rectangle with rounded corners is represented in outline in FIG. 2. The height-to-width ratio of the cross section of the portion CC is therefore from 1:1.5 to 1:4 and in particular 1:2. Specifically, it is conceivable for the height of the cross section of the portion C to be 0.3 mm and for the width to be 0.6 mm, the diameter of the wire 18 being from 0.4 mm to 0.6 mm, preferably 0.5 mm. The effect of this is that the wire 18 is wider in the portion CC than the portions L1, L2, R1 and R2 in the lateral view according to FIG. 2 and narrower in the frontal view according to FIG. 3. This deformation of the portion CC leads to the electric field strength being particularly high, especially on the rounded corners, with the effect that the plasma which is generated by the radiofrequency alternating voltage is ignited at least almost exclusively on these rounded corners of the portion CC. That is to say, the plasma is generated in a locally very defined way and reliably, and reliable and expedient treatment of the tissue is therefore possible. Furthermore, the flattened shape of the portion CC proves particularly suitable for manipulating tissue during the use of the resectoscope 10 as described above. A further advantage may be that the wear of the electrode due to the plasma is distributed over the round corners of the portion CC and therefore has no further effects on the functionality of the electrode 16.

According to another exemplary embodiment of the invention, not only may the portion C have a radius, that is to say a loop shape, but the adjacent portions R2 and L2 may also have a radius and be aligned toward one another in order to counteract the loop-like shape of the portion C. By this slight angulation of the portions R2 and L2, any further radii of curvature of the electrode 16 may be minimized in order to concentrate the plasma onto the portion CC.

According to another possible exemplary embodiment of the invention, the flattened region of the portion C, that is to say the portion CC, may be limited to an angle range w of from 110° to 160° between the portions R1 and L1 (in the portion C). It is especially conceivable for only a very narrow region of the portion C to be flattened. For example, this appears to be advantageous for certain applications. For instance, it is conceivable for the operator to be provided with a set of different electrodes 16 with flattened portions CC having different widths, which may be selected and coupled to the resectoscope 10 according to the intended use.

LIST OF REFERENCE SIGNS

10 resectoscope
11 resectoscope shaft
12 outer shaft
13 inner shaft
14 electrode carrier
15 optics
16 electrode
17 guide element
18 wire
19 handle
20 slide
21 grip part
22 grip part
23 spring bridge
24 eyepiece
R1 first portion
R2 second portion
L1 first portion
L2 second portion
C central portion
CC flattened portion
α angle
ω angle

The invention claimed is:

1. An electrode for an electrosurgical handheld instrument comprising:

a wire including:

a first proximal end and a second proximal end both being configured to connect to an electrode carrier of the electrosurgical handheld instrument;

a first proximal portion being adjacent to the first proximal end and a second proximal portion being adjacent to the second proximal end, the first proximal portion being parallel and rectilinear to the second proximal portion;

a first distal portion being adjacent to the first proximal portion and a second distal portion being adjacent to the second proximal portion, and the first distal portion and the second distal portion both being configured to be connected by a central portion;

a flattened portion provided at the central portion, wherein:

the first proximal portion, the second proximal portion, the first distal portion, and the second distal portion have a round or circular cross section;

the flattened portion has a cross section with rounded corners, the flattened portion forming a continuous contour, the cross section being one of an oval, elliptical or rectangular shape;

the cross section of the flattened portion having a height-to-width ratio from 1:1.5 to 1:4; and transitions between the round or circular cross section and the oval, elliptical, or rectangular cross section with rounded corners are made so smooth that radii of curvature are not formed at these transition points which are smaller than a smallest radius curvature of the central portion.

2. The electrode for the electrosurgical handheld instrument as claimed in claim 1, wherein:

the central portion has a radius of from 2.8 mm to 3.5 mm;

the central portion is rectilinear to the first distal portion and the second distal portion;

the central portion is aligned at a right angle to the first distal portion and the second distal portion; or the central portion has a V-shape.

3. The electrode for the electrosurgical handheld instrument as claimed in claim 1, wherein the first distal portion and the second distal portion have a radius or are aligned parallel to one another and transitions between the first proximal portion, the second proximal portion, the first distal portion, and the second distal portion and between the central portion; and the first distal portion and the second distal portion have a radius.

4. The electrode for the electrosurgical handheld instrument as claimed in claim 1, wherein the wire has a diameter of from 0.4 mm to 0.6 mm.

5. The electrode for the electrosurgical handheld instrument as claimed in claim 1, wherein the cross section of the flattened portion has a height-to-width ratio of from 1:2.

6. The electrode for the electrosurgical handheld instrument as claimed in claim 1, wherein the cross section of the flattened portion has a height of 0.3 mm and a width of 0.6 mm.

7. The electrode for the electrosurgical handheld instrument as claimed in claim 1, wherein the flattened portion includes an angle ω of from 110° to 160°.

8. The electrode for the electrosurgical handheld instrument as claimed in claim 1, wherein the wire consists of tungsten, stainless steel, platinum-iridium, titanium, a titanium alloy or a platinum-tungsten alloy.

9. The electrode for the electrosurgical handheld instrument as claimed in claim 1, wherein lengths of the first distal portion and the second distal portion are from 0.7 mm to 1.7 mm.

10. The electrode for the electrosurgical handheld instrument as claimed in claim 1, wherein the first distal portion and the second distal portion include an angle α of from 35° to 120° with the first proximal portion and the second proximal portion.

11. The electrode for the electrosurgical handheld instrument as claimed in claim 1, wherein the first distal portion, the second distal portion, the central portion, and the flattened portion lie in a plane.

* * * * *